United States Patent [19]

Ong et al.

[11] Patent Number: 5,669,502

[45] Date of Patent: Sep. 23, 1997

[54] VIAL HOLDER

[75] Inventors: Holly Ong, Redwood City; Paul Schmid, San Francisco, both of Calif.; Cliff Wood, Pound Ridge; David G. Bragin, Brooklyn, both of N.Y.

[73] Assignee: Berlex Laboratories, Inc., Cedar Knolls, N.J.

[21] Appl. No.: 422,829

[22] Filed: Apr. 17, 1995

[51] Int. Cl.⁶ .................................................. B65D 1/09
[52] U.S. Cl. ........................... 206/528; 206/530; 206/438; 206/446; 604/403
[58] Field of Search ............................ 206/438, 363, 206/446, 222, 528, 530, 538, 539; 141/383, 386; 604/403

[56] References Cited

U.S. PATENT DOCUMENTS

| | | | |
|---|---|---|---|
| 2,555,863 | 6/1951 | Slaughter | 206/530 |
| 2,977,014 | 3/1961 | Kock | 206/530 |
| 3,397,694 | 8/1968 | Ogle | 206/222 X |
| 3,444,991 | 5/1969 | Raybois | 206/530 |
| 3,720,341 | 3/1973 | Greenfield et al. | 206/530 |
| 3,977,555 | 8/1976 | Larson | 206/363 X |
| 4,475,915 | 10/1984 | Sloane | 604/414 |
| 4,957,385 | 9/1990 | Weinstein | 206/530 X |
| 5,240,047 | 8/1993 | Hedges | 141/21 |
| 5,247,972 | 9/1993 | Tetreault | 141/27 |
| 5,393,497 | 2/1995 | Haber et al. | 206/528 X |

FOREIGN PATENT DOCUMENTS

| | | |
|---|---|---|
| 2052992 | 2/1981 | United Kingdom . |
| 2274443 | 7/1994 | United Kingdom . |

*Primary Examiner*—Paul T. Sewell
*Assistant Examiner*—Tara L. Laster
*Attorney, Agent, or Firm*—Millen, White, Zelano & Branigan, P.C.

[57] ABSTRACT

A vial holder is provided which is easily loaded with a vial, retains the vial in a rigid manner and permits the vial to be discharged in a simple manner. The vial holder can also exhibit two vial retention sections for simultaneously rigidly holding two vials.

33 Claims, 5 Drawing Sheets

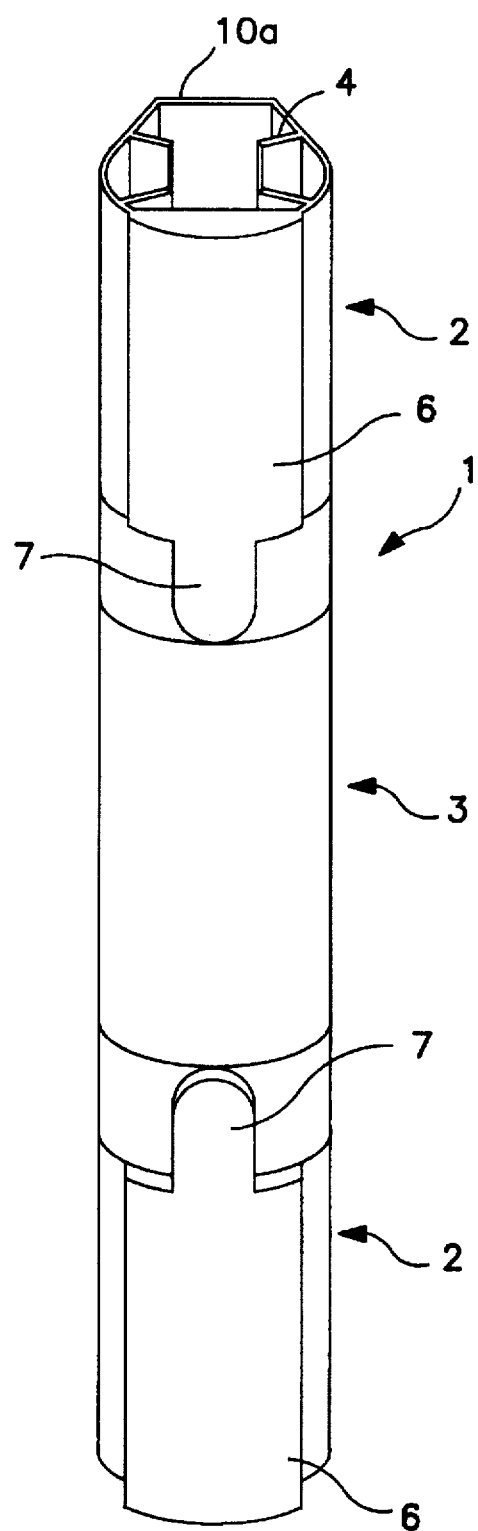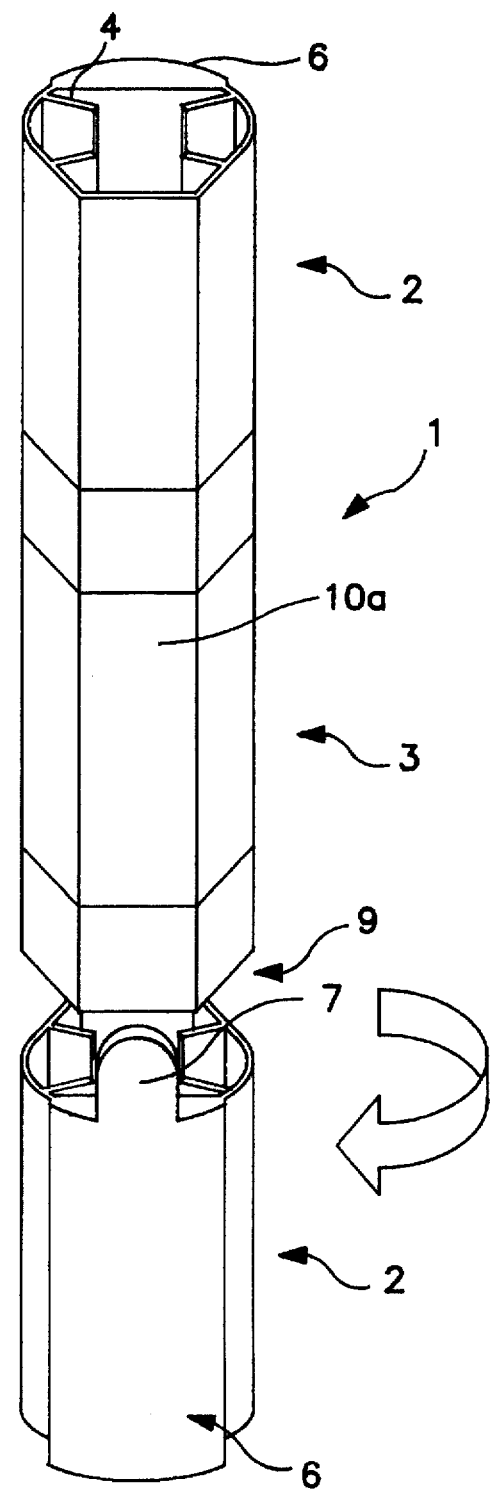
FIG. IA          FIG. IB

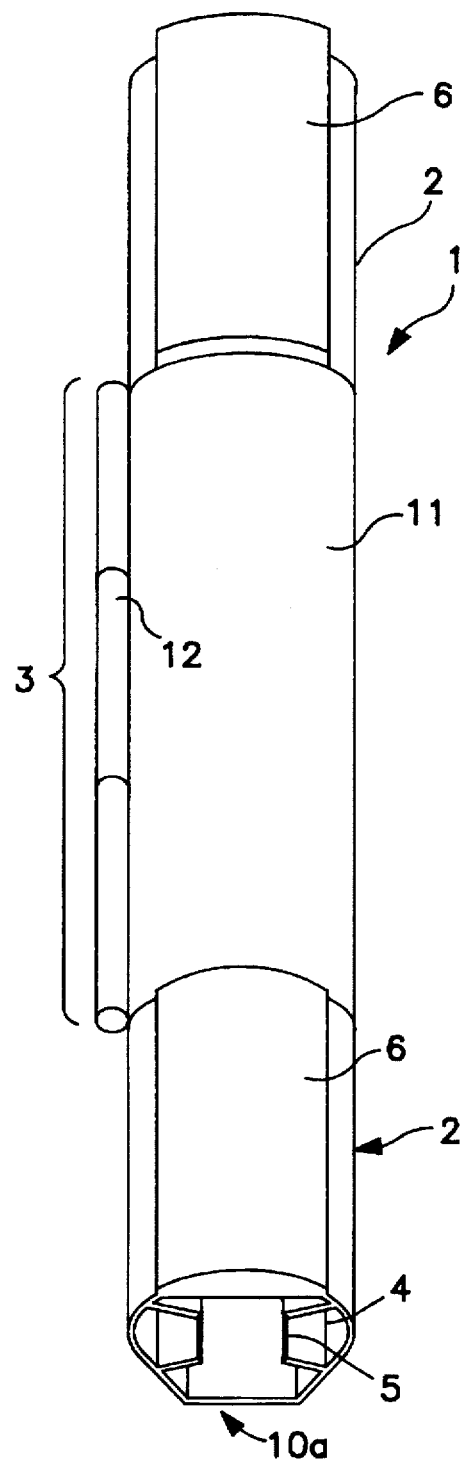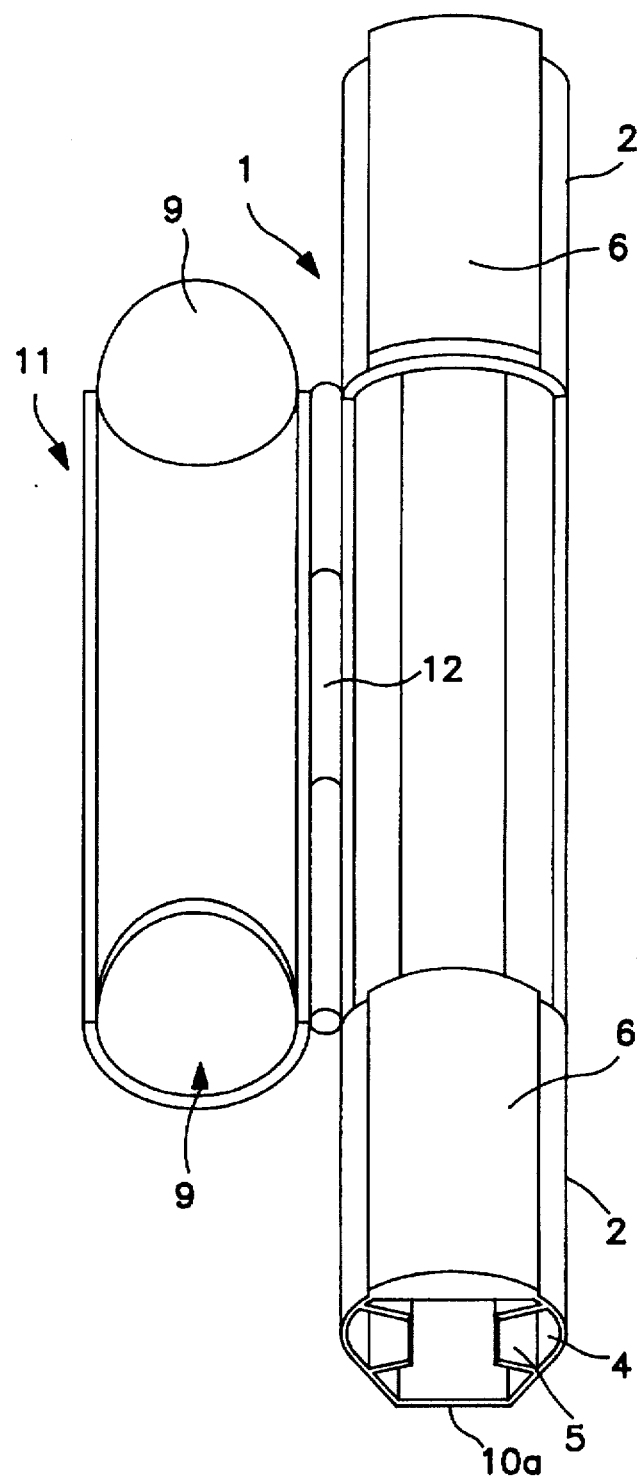
FIG. 4A                    FIG. 4B

VIAL HOLDER

SUMMARY OF THE INVENTION

The invention relates to a device for holding small vials such as used in the administration of pharmaceuticals. In particular, the invention relates to a vial holder for facilitating the withdrawal of fluid from a vial to a syringe and/or the introduction of fluid into a vial from a syringe.

The injection of medicaments via syringe is a common everyday occurrence in the medical profession. Typically, a small vial containing a single dose of a drug is held in one hand, and a syringe is held in the other. By inserting the needle of the syringe through the septum covering the mouth of the vial, fluid can be withdrawn from the vial into the syringe, e.g., by pulling out the plunger of the syringe. The risks associated with this conventional technique are readily apparent. While holding the vial in one's hand, an attempt to insert the needle through the septum can easily result in the needle missing the intended mark and injuring the user, especially when the smaller medical vials, e.g., 3 cc, are used. With the rising fears of transmission of viral infections, such accidental injuries with the syringes are an important concern in the medical field.

Also, in an effort to have patients such as diabetics lead as normal a life as possible without the continuous need for visits to medical professionals, it is increasingly common for drugs to be made available in a form for self-administration. In such cases, the patient is provided with small vials of a drug, as well as syringes for removing the drug from the vial and thereafter self-administering the drug by injection.

Many patients who used such self-administering formulations experience great difficulty in handling the small vials, e.g., 5 cc and 3 cc vials, and performing the manipulative tasks required for loading the syringe and administering the drug. Such difficulty can stem from, for example, reduced dexterity or poor eyesight either due to the particular disease from which they are suffering or due to advanced age. To aid such patients, vial holder devices have been developed which ease handling of the vials and alignment of the syringe with the vial, thereby facilitating withdrawal and administration of drugs.

Tetreault (U.S. Pat. No. 5,247,972) discloses an alignment guide device for hypodermic syringes to facilitate withdrawing fluid samples from a bottle. The device comprises a tubular housing and an inner tube positioned within the tubular housing. One end of the inner tube has a flange and a mounting element which extends from the flange. The mounting element contains grooves into which the flange of a hypodermic syringe can be fitted. At the other end, the inner tube is provided with finger-like protrusions having beveled tips and indentations for engaging a liquid-containing bottle in a snap-fit arrangement. The tubular housing is provided with a magnifying lens integral with its outer surface to enhance visualization of a syringe positioned within the inner tube, thereby enhancing the accuracy of withdrawing specific volumes of liquid from the bottle.

Hedges (U.S. Pat. No. 5,240,047) discloses a unitary one-piece needle-guide and bottle-holder device. The bottle-holder portion of the device is of a cylindrical shape having slots running the length thereof, so as to visualize the contents of a bottle positioned in the bottle-holder portion. The walls of this portion of the device exhibit sufficient elasticity so that they can be slidably expanded when a bottle is fitted therein and provide a good friction fit between the vial and the bottle-holder portion. The device further contains a syringe-guide portion which is also of cylindrical shape but of smaller diameter than the bottle-holder portion. A connecting channel is provided between the bottle-holder portion and the syringe-guide portion so that, when a syringe is positioned within the latter, the needle can extend through the connecting channel and penetrate into the vial through its cap.

A further syringe and vial holder is described by Sloane (U.S. Pat. No. 4,475,915). The device has a trough-like section for receiving a vial. A wall member is positioned adjacent the trough-like section with an aperture therein for supporting a syringe and permitting a syringe's needle to project into the trough section where it can penetrate into a vial contained therein. Further, a rest member is provided which is spaced from the wall member and has an aperture for receiving and supporting a syringe.

While the devices within the prior art often facilitate manipulation of a syringe and vial during withdrawal of fluid from the vial, they do not adequately and safely retain the vial within the device nor do they permit easy removal of the used vial. Thus, the need still exists for a vial holder which can be easily loaded with a vial, provides rigid retention of the vial during the transfer of fluid, and permits quick and easy removal of the empty vial from the vial holder.

Furthermore, the prior art devices do not provide a means for rigidly holding two separate vials. Some pharmaceutical preparations are prepared by removing a diluent from a first vial and introducing the diluent into a second vial containing, for example, a solid pharmaceutical such as a lyophilized powder to be dissolved in the diluent. Thereafter, the resultant mixture can be removed from the second vial for administration. Single vial holder devices would require several manipulative steps including exchange of the vials to completely formulate the medicament and administer same. The additional manipulation steps increase the risk of injury by the syringe needle and exacerbates the difficulties experienced by patients with poor eyesight and/or limited dexterity.

Therefore, an object of the present invention is to provide a vial holder which is easily loaded with a vial, retains the vial in a rigid manner and permits the vial to be discharged in a simple manner. A further object is to provide a vial holder which is capable of simultaneously rigidly holding two vials.

Upon further study of the specification and appended claims, further objects and advantages of this invention will become apparent to those skilled in the art.

In accordance with one embodiment of the invention, these objects are achieved by a vial holder comprising:

- a handle portion, preferably substantially cylindrical in shape, having a longitudinal axis, a first end and a second end, wherein at least the first end of the handle is provided with a wall member;

- a hollow vial retention section, attached to the first end of the handle portion, the vial retention section having a longitudinal axis, a substantially cylindrically shaped internal wall, a first open end adjacent the first end of the handle portion, and a second open end; and

- at least one retention member for preventing passage of a vial, when positioned within the vial retention section, through the second open end of the vial retention section;

wherein the vial retention section is movable between a first position, in which its longitudinal axis is substantially aligned with the longitudinal axis of the handle portion and a second position in which its longitudinal axis is displaced from that of the handle portion providing access into the hollow interior of the vial retention section for introduction of a vial.

To help in positioning the vial, the vial retention section can be provided with a plurality of aligning members positioned on the internal wall of the vial retention section. Also, to provide for the retention of a second vial, the above embodiment can be further provided with a second movable vial retention section, equipped with aligning elements and at least one retention member, attached to the second end of the handle portion. In such a case, the second end of the handle portion is also provided with a wall member.

According to a further embodiment, the objects of the invention can be achieved by a vial holder comprising:

a housing, preferably substantially cylindrically shaped, having a handle portion, a hollow vial retention section and longitudinal axis, the vial retention section is positioned at one end of the housing and has a substantially cylindrically shaped internal wall, a first end and a second open end;

at least one retention member for preventing passage of a vial, when positioned within the vial retention section, through the second open end;

a door in the outer wall of the housing and connected to the housing by a hinge, wherein, when the door is in an open position, access is provided into the interior of the vial retention section for introduction of a vial; and a retaining wall member which separates the vial retention section from the handle portion when the door is in a closed position, a vial retention zone being defined between the second open end of the vial retention section and the retaining wall member.

As with the first embodiment, this embodiment of the vial holder can also have a plurality of aligning members positioned on the internal wall of the vial retention section for aligning the vial within the vial retention section. Further, this second embodiment can also be provided with a second vial retention section equipped with its own aligning elements and at least one retention member, positioned at the other end of the handle portion. In such a case, a second retaining wall member is provided which separates the second vial retention section and handle portion and thereby defines a second vial retention zone.

In the first embodiment described above, the vial retention section is movably attached to the handle portion. During loading of a vial into the vial retention section, the longitudinal axis of the latter is displaced from the longitudinal axis of the handle portion, thereby providing access to the hollow interior of the vial retention section. In this open position, a vial can easily be inserted into the vial retention section. The vial is introduced through the first open end of the vial retention section.

Typical vials containing drugs have a bottom region of a certain diameter, a vial head of a smaller diameter with a shoulder region connecting the two. The mouth of the vial is sealed by an elastomeric seal or septum which can be punctured by the needle of a syringe. For purposes of maintaining sterility, a seal is typically provided over the mouth of the vial, covering the elastomeric seal or septum to prevent contamination thereof.

The aligning members help to align the longitudinal axis of the vial substantially with the longitudinal axis of the vial retention section. Passage of the vial out of the second open end of the vial retention section is prevented by the at least one retention member. Preferably, the at least one retention member is positioned adjacent the second open end of the vial retention section and engages the shoulder portion of the vial. As a result, the vial head protrudes out of the vial holder device through the second open end of the vial retention section.

Once the vial is positioned, the vial retention section with the vial contained therein can be moved back into a closed position wherein the longitudinal axis of the vial retaining section, as well as the vial, is substantially aligned with the longitudinal axis of the handle portion. In this position, the vial is snugly held between the at least one retention member and the wall member of the first end of the handle portion. By holding the handle portion, a user can insert a syringe needle through the open end of the vial retention section, and penetrate the elastomeric seal or septum to permit the withdrawal of fluid from the vial into the syringe or the introduction of fluid into the vial from the syringe. Since the handle portion is much larger and easier to grip than the small vial itself, the transfer of fluid between the vial and the syringe is much easier to perform. Also, since the vial itself is not held within the user's hand, the risk of injury from the syringe needle is reduced.

In addition, when, as described above, the head and mouth of the vial extends through the second open end of the vial retention section, the user can delay removing the sterility seal covering the septum until after the vial is loaded into the vial holder. Thus, the sterility seal can be removed just prior to the insertion of the syringe's needle through the vial's septum. This eliminates the need to manually handle the vial after removal of the sterility seal and lessens the risk of contamination.

To remove the vial from the vial holder, the user need only move the vial retention section back to a position in which the longitudinal axis thereof is displaced from the longitudinal axis of the handle portion. The vial is then easily discharged by gravity or by pushing on the top of the vial through the second open end of the vial retention section.

The aligning members are in general any structural feature which can engage and align the vial so that its longitudinal axis is substantially aligned with that of the vial retention section. The mouth of the vial is preferably easily accessible through the second open end of the vial retention section to allow for the syringe needle to penetrate the septum. In particular, the aligning means are any type of outward protrusion which extend from the internal wall of the vial retention section and are capable of aligning the vial in the manner described above. Preferably, the aligning members also aid in holding the vial in a rigid manner by preventing radial movement within the vial retention section.

In a preferred embodiment, each of the alignment members is in the form of a positioning vane. The vanes extend from the internal wall of the vial retention section and have a longitudinal axis substantially parallel with the longitudinal axis of the vial retention section.

As for the at least one retention member, this structure can be any element which engages the top portion of the vial, and thereby prevents it from passing out through the second open end of the vial retention section. Preferably, the retention member also aids in aligning the mouth of the vial with the second open end to provide easy access to the vial septum for the syringe needle. It is especially advantageous for the retention member to engage the shoulder of the vial and permit the mouth of the vial to extend out the vial retention section.

In accordance with a preferred embodiment, the retention members are protrusions or tabs which extend out from the internal wall of the vial retention section and are located at the end of each of the positioning vanes used as aligning members. Preferably, the tabs are of such a length that they permit the passage of the mouth of the vial through the second open end of the vial retention section and engage the shoulder of the vial.

Movement of the vial retention section between the open and closed positions can be achieved through a variety of mechanisms known within the art. In accordance with a preferred embodiment, the vial retention section is attached to the first end of the handle portion via a pivot hinge. The vial retention section is rotatable about the pivot hinge and thereby can move from a first closed position in which its longitudinal axis is substantially aligned with the longitudinal axis of the handle portion to a second open position in which its longitudinal axis is substantially parallel with that of the handle portion. In addition, the vial retention section is preferably provided with a locking element so that, when the axis of the vial retention section is aligned with that of the handle portion, the section is locked into the closed position. This facilitates handling during the syringe needle's penetration of the vial septum by preventing movement of the vial retention section relative to the handle.

In the second embodiment described above, instead of providing access to the interior of the vial retention section by movement of the latter relative to the handle portion, the vial holder is provided with a door which, when open, provides a user with access into the interior of the vial retention section.

As with the prior embodiment, the vial retention section can be provided with aligning members for substantially aligning the longitudinal axis of the vial with that of the handle. The vial retention section also has at least one retention member to prevent passage of the vial out of the second open end of the vial retention section. The alignment members are preferably positioning vanes along the internal wall of the vial retention section. The at least one retention member is preferably a plurality of tabs or protrusions, one positioned at the end of each positioning vane, which engage the shoulder of a vial, preventing it from passing out of the vial retention section but permitting the mouth of the vial to extend out the open end.

To rigidly retain the vial in the vial retention section of the second embodiment, the vial holder is provided with a retaining wall member. When a vial is positioned in the vial retention section and the door is closed, the vial is held between the at least one retention member and the retaining wall member. Preferably, the door is positioned in the handle portion below the vial retention section and the wall member is attached to the door on its inner surface, i.e., the surface facing the interior of the housing. Further, the first end of the vial retention section is open. Thus, when the door is open, a vial can be inserted into the vial retention section through the open first end thereof. Once a vial is positioned in the vial retention section and the door is subsequently closed, the wall member attached to the door acts in conjunction with the at least one retention member to rigidly hold the vial within the vial in place.

In addition to the features described above, both embodiments of the vial holder can be provided with further modifications to, for example, facilitate retaining of the vial within the vial holder section, facilitate loading of the vial, stabilize the vial holder when placed on a flat surface and enhance visualization of the vial.

For example, for enhancing the visibility of the vial, the vial retention section at the end of the vial holder can be made of a transparent material, e.g., glass or plastic. Alternatively or in addition to the transparent vial retention section, this section can also be provided with a magnifying lens as part of the structure of the vial retention section. By having that portion of the vial holder which retains the vial be transparent and/or provided with a magnifying lens, a user can observe the introduction or removal of liquid from the vial. Thus, for example, if liquid is to be introduced into a vial containing a solid pharmaceutical to dissolve the latter, the user, through the transparent housing and/or magnifying lens, can see the introduction of the diluent into the vial and observe the dissolution of the solid pharmaceutical. Also, in the case of small volume vials, such as 3 cc vials, the magnifying lens makes the vial label easier to read, thereby aiding those patients with poor eyesight in identifying the contents of the vial.

The vial retention section may also be provided with one or more resilient spring members which, when a vial is positioned in the vial retention section, apply pressure to the outside of the vial, thereby providing a pressure fit or friction fit of the vial within the vial retention section. Thus, when, e.g., in the first embodiment, the vial retention section is in an open position and the vial is no longer rigidly held between the at least one retention member and the wall member, the spring elements can maintain a friction fit of the vial within the vial retention section, thereby preventing the vial from falling out. Since the spring elements retain the vial only by a pressure fit or friction fit, the vial can still be easily removed from the vial retention section by pushing on the mouth of the vial through the second open end of the vial retention section.

In the second embodiment, when the wall member is attached to the door and the door is opened, thereby preventing the vial from being rigidly held between the at least one retention member and the wall member, the spring elements can provide a similar friction fit to retain the vial within the vial retention section.

To aid in the introduction of a vial into the vial retention section, the vial holder can be provided with a channel structure. Thus, by sliding the vial along the channel, the loading of the vial is simplified. In the first embodiment discussed above, the channel structure can be provided on the outer surface of the handle portion so that, when the vial retention section is in an open position, a vial can be placed on the channel with its mouth pointed in the direction of the interior of the vial retention section. Sliding the vial along the channel loads the vial into the vial retention section where the at least one retention member engages the vial, thereby preventing the vial from moving out the open end.

In the second embodiment discussed above, a similar channel means can be provided within the interior of the tubular housing. So, for example, when the door having the wall member connected thereto is open, a vial can be placed within the vial holder on the internal channel so that the mouth of the vial faces the vial retention section. By sliding the vial toward the vial retention section, the vial is loaded and the at least one retention member engages the vial preventing passage out the open end.

While the overall outer surface of the vial holder is preferably cylindrical in shape, thereby facilitating grasping of the vial holder, a portion of the outer surface can be provided with a stabilizing shape which will permit the vial holder to rest on a flat surface without rolling. For example, a portion of the outer surface can be a flat or concave surface so that when, placed on a flat surface, the flat or concave surface portion will prevent the vial holder from rolling. This stabilizing effect is particularly advantageous in those situations where the user's condition renders him or her incapable of grasping the vial holder for long time periods.

In a particularly preferred modification, the first embodiment described above is provided with a concave channel on the outer surface of both the handle portion and the vial retention section(s). In this case, when the vial retention section(s) is in a closed position, the concave channel of the vial retention section(s) is aligned with the concave channel in the handle portion. This concave structure also provides a stabilizing structure so that when the vial holder is placed on a flat surface, the vial holder is prevented from rolling. Conversely, when the vial retention section is in an open position, the concave channel on the handle portion provides a channel structure to facilitate the loading of a vial. The concave channel in the outer surface of the vial holder also facilitates gripping of the vial holder by providing a thumb rest.

In accordance with a further aspect of the invention, the vial holder can form part of a kit. Such a kit would contain in combination, for example, a vial holder in accordance with the invention, one or more vials, and one or more syringes. The one or more vials could contain a pharmaceutical ready for use or at least one vial of a pharmaceutical and at least one other vial of a diluent, or could contain empty vials and thus be used for training potential users in the handling and operation of the vial holder.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIGS. 1A and 1B illustrate a first embodiment of the vial holder according to the invention;

FIGS. 4A and 4B illustrate a further embodiment of the vial holder; and

DETAILED DESCRIPTION

FIGS. 1A and 1B illustrate a vial holder 1 in accordance with a first embodiment of the invention. FIG. 1A shows a front view of the vial holder, while FIG. 1B shows a back view.

Figure 2A:
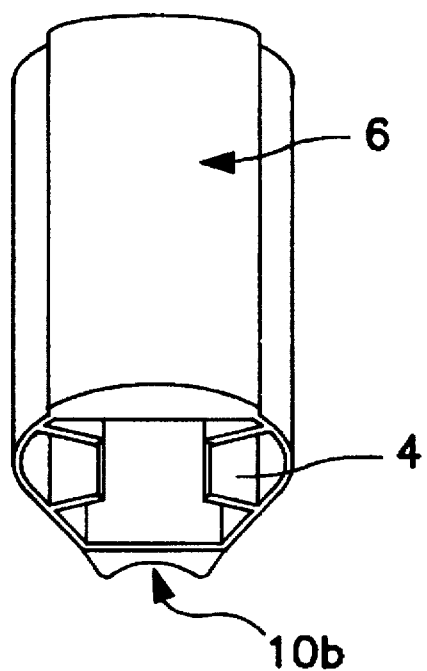
FIGS. 2A and 2B illustrate further features of the vial holder.
Figure 2B:
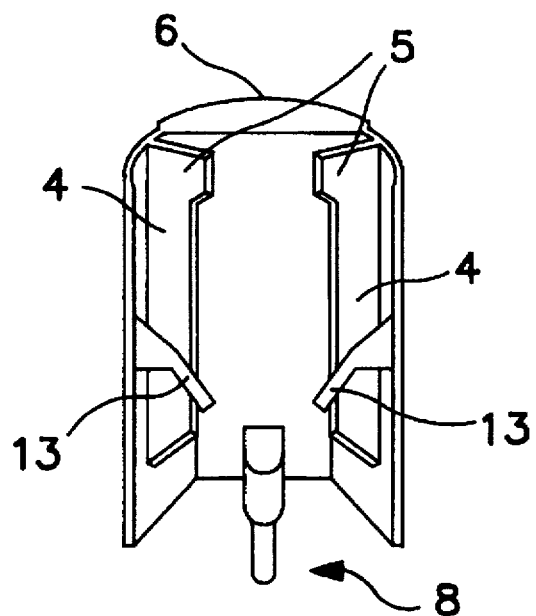

The embodiment shown in FIGS. 1A and 1B has vial retention sections 2 at both ends of the handle portion 3. As can be seen through the second open end of the top vial retention section, the internal surface of the vial retention section is substantially cylindrical and is provided with, for example, 3 or 4 positioning vanes 4 along the surface thereof. As shown in FIG. 2B, at the end of the positioning vanes adjacent the second open end of the vial retention section, there are projections or tabs 5 which are the retention members for preventing the vial from passing out through the open end.

The front surfaces of the vial retention sections are provided with a magnifying lens 6 so that, when a vial is positioned within a vial retention section, the transfer of fluid into and out of a vial is easily observed by the user. Also, the vial retention section 2 itself is preferably made of a transparent material allowing the user to see the vial positioned therein. Suitable materials are, for example, glass and clear plastics such as polycarbonate, polyethylene terephthalate (PET), e.g., Eastman PETG #6753, or polysulfone. The handle portion can be made of transparent or opaque material. Further, the outer surface of the handle portion can be textured so as to facilitate gripping of the vial holder by the user. If desired, the materials selected for making the vial holder can be chemically resistant and/or heat resistant, for example, for withstanding sterilization procedures. The vial holder can be manufactured in accordance with known techniques such as injection molding with separate parts being sonically welded together or snapped together.

Extending from the magnifying lens is a locking tab 7. The locking tab 7 has a protrusion extending from the surface which faces the handle portion. The handle portion 3 is provided with a recess capable of engaging the protrusion from the locking tab in a snap-fit arrangement.

In the embodiment illustrated in FIGS. 1A and 1B, the vial retention section is pivotally attached to the handle portion by a molded-in pivot pin 8. See FIG. 2B. Pivotal attachments can be provided by a variety of means such as a snap-fit arrangement. The pivot pin can extend into a receptacle provided in the handle, for example, a cylindrically-shaped pocket in a solid handle. The pin is held in the receptacle by a projection extending into a recess of the pin or vice versa so that the pin can freely rotate within the receptacle.

Thus, by an easy twisting motion or by applying pressure against the raised magnifying lens or locking tab in a direction perpendicular to the longitudinal axis of the handle portion, the vial retention section can pivot to an open position as shown by the arrow in FIG. 1B. In this open position, a vial can be introduced into the first open end of the vial retention section. The movement of the vial into the vial retention section is eventually stopped due to the engagement of vial shoulder by the retention members 5 adjacent the second open end of the vial retention section. The ends of the handle portion are provided with a wall member 9 so that, by rotating the vial retention section containing a vial back into the closed and locked position as illustrated in FIG. 1A, the vial is rigidly retained within the vial retention section between the retention members engaging the shoulder of the vial and the wall member of the handle portion. Furthermore, to add weight to the vial holder so that it is more comfortably held within the hand, the handle portion is preferably solid.

Figure 3A:
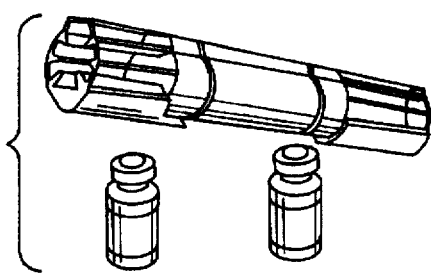
FIGS. 3a-3g illustrate operation of the vial holder.
Figure 3B:
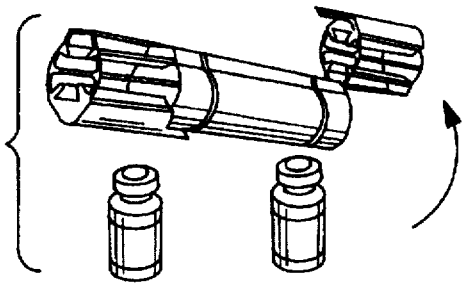
Figure 3C:
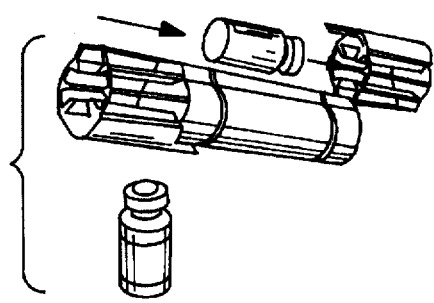
Figure 3D:
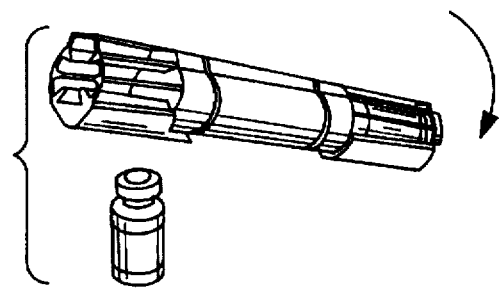
Figure 3E:
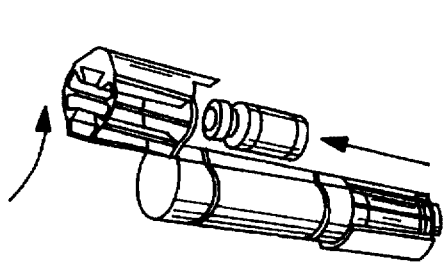
Figure 3F:
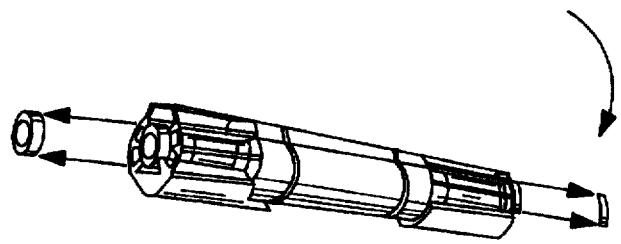
Figure 3G:
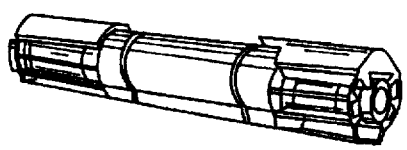
Figure 5:
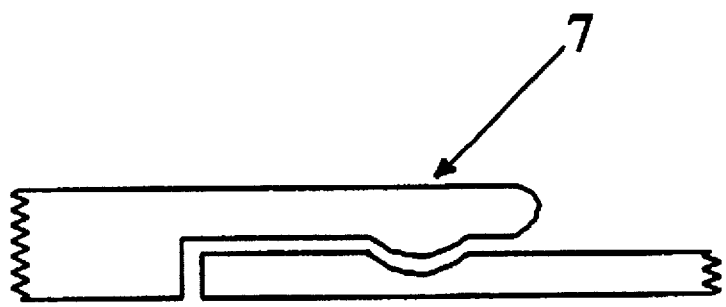
FIG. 5 illustrates a cross-section view of a locking tab and an associated locking protrusion.

The back surface of the vial holder is provided with a flat surface 10a (see FIGS. 1A and 1B) or a concave surface 10b (see FIG. 2A) which acts as a stabilizing structure to prevent the vial holder from rolling when placed on a flat surface. Also, this structure can function as a channel to facilitate loading of a vial into the vial retention section. See FIGS. 3c and 3e.

FIGS. 3a-3g demonstrate operation of this embodiment of the vial holder. Initially, the vial retention sections at each end of the handle portion of the vial holder are in a closed position. By rotating one of the vial retention sections about its pivot hinge, the vial retention section is moved to a position in which its longitudinal axis is substantially parallel with that of the handle portion and so that the interior of the vial retention section is aligned with the channel structure on the back surface of the handle portion. By sliding a vial along the channel structure, the vial is inserted into the vial retention section until it engages the retention members. Thereafter, the loaded vial retention section is again rotated about the pivot hinge and brought back into a closed position, wherein the protrusion of the locking tab engages the recess on the front surface of the handle portion.

The steps are then repeated for the other vial retention section, resulting in each vial retention section rigidly holding a vial. Safety caps covering the septums of the vials to prevent contamination can then be removed to permit the introduction of a syringe needle through the septum. Finally, when the vial holder is not being held, the flat or concave structure on the back side of the handle portion and vial retention sections provides a stabilizing means to prevent the vial holder from rolling.

FIGS. 4A and 4B illustrate a second embodiment of the vial holder 1 in accordance the invention. As shown in FIGS. 4A and 4B, this embodiment can also be provided with two vial retention sections, one at each end of the vial holder.

In this embodiment, the vial retention sections 2 are not movable with respect to the rest of the vial holder. In this embodiment, access into the interior region of the vial retention section is provided by a door 11 attached by hinge 12. In the particular embodiment illustrated in FIGS. 4A and 4B, the door is provided in the handle portion 3. When the door 11 is open, vials can be placed within the interior of the handle portion 3 and from there introduced into the vial retention sections 2 until the retention members 5 in the vial retention section engage the vial, preventing it from passing through the open end. A channel structure can be provided within the interior of the vial holder to facilitate the loading of the vial into the vial retention section.

In this particular embodiment, in which the door is in the handle portion, retaining wall members 9 are attached to the inside surface of the door. When a vial is loaded into a vial retention section 2 and the door is closed, wall member 9 acts in conjunction with the retention members 5 in the vial retention section to rigidly retain the vial. The door can also be provided with a locking structure similar to that in the embodiment illustrated in FIGS. 1A and 1B so that, for example, when the door is in a closed position the locking structure engages the outer surface of the vial holder in a snap-fit arrangement.

In both the above embodiments, the vial retention section is provided with a magnifying lens 6 to enable the user to observe the vial during the introduction or withdrawal of fluid from the vial via a syringe. Also, the internal surface of the vial retention sections can be provided with resilient spring members 13 (see FIG. 2B) which provide a friction fit with the vial when it is loaded into a vial retention section.

The preceding can be repeated with similar success by substituting the generically or specifically described reactants and/or operating conditions of this invention for those used therein.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A vial holder comprising:
   a handle portion having a longitudinal axis, a first end and a second end, wherein at least said first end of said handle portion is closed by a wall member;
   a hollow vial retention section having a hollow interior, attached to said first end of said handle portion, said vial retention section having a longitudinal axis, a substantially cylindrically shaped internal wall, a first open end adjacent said first end of said handle portion, and a second open end;
   at least one retention member for preventing passage of a vial, when positioned within said vial retention section, through said second open end of said vial retention section; and
   means for displacing said wall member of said handle portion and said vial retention section from one another whereby access is provided into the hollow interior of said vial retention section for introduction of a vial.

2. A vial holder according to claim 1, wherein said handle portion is substantially cylindrically shaped.

3. A vial holder according to claim 1, further comprising a plurality of aligning elements positioned on said internal wall of said vial retention section for the alignment of a vial within said vial retention section.

4. A vial holder according to claim 3, wherein said plurality of aligning elements are a plurality of positioning vanes which extend in the direction of the longitudinal axis of said vial retention section.

5. A vial holder according to claim 1, wherein said vial retention section is transparent.

6. A vial holder according to claim 1, further comprising a magnifying lens integral with said vial retention section.

7. A vial holder according to claim 1, wherein said handle portion exhibits a concave surface extending in the direction of said longitudinal axis of said handle portion.

8. A vial holder according to claim 1, wherein said handle portion exhibits a flat surface extending in the direction of said longitudinal axis of said handle portion.

9. A vial holder according to claim 1, wherein means for displacing is provided by a pivotal hinge connecting said vial retention section with said handle portion, whereby said vial retention section is pivotally attached to said handle portion to permit access into the interior of said vial retention section through said first open end.

10. A vial holder according to claim 9, further comprising a locking tab extending from said first end of said handle portion, said locking tab having a locking protrusion and said handle portion having a recess in the external surface thereof adjacent said first end of said handle portion for receiving said locking protrusion in snap-fit arrangement.

11. A vial holder according to claim 1, further comprising spring elements attached to the internal wall of said vial retention section wherein said spring elements are capable of engaging a vial positioned within said vial retention section.

12. A vial holder according to claim 1, further comprising:
    a second hollow vial retention section having a hollow interior attached to said second end of said handle portion, said second end of said handle portion being closed by a second wall member, said second hollow vial retention section having a longitudinal axis, a substantially cylindrically shaped internal wall, a first open end adjacent said second end of said handle portion and a second open end;
    at least one additional retention member for preventing passage of a vial, when positioned within said second vial retention section, through said second open end of said second vial retention section; and means for displacing said second wall member of said handle portion and said second vial retention section from one another whereby access is provided into the hollow interior of said second vial retention section for introduction of a vial.

13. A vial holder according to claim 2, further comprising:

a second hollow vial retention section having a hollow interior attached to said second end of said handle portion, said second end of said handle portion being closed by a second wall member, said second hollow vial retention section having a longitudinal axis, a substantially cylindrically shaped internal wall, a first open end adjacent said second end of said handle portion and a second open end;

at least one additional retention member for preventing passage of a vial, when positioned within said second vial retention section, through said second open end of said second vial retention section; and means for displacing said second wall member of said handle portion and said second vial retention section from one another whereby access is provided into the hollow interior of said second vial retention section for introduction of a vial.

14. A vial holder according to claim 13, further comprising:

a plurality of aligning elements positioned on said internal wall of said vial retention section for the alignment of a vial within said vial retention section; and a plurality of additional aligning elements positioned on said internal wall of said second vial retention section for alignment of a vial within said second vial retention section.

15. A vial holder according to claim 1, wherein said handle portion is hollow and said means for displacing comprises:

a door in said handle portion, connected thereto by a hinge and said wall member of said handle portion is connected to said door, wherein, when said door is in an open position, access is provided into the interior of said vial retention section for introduction of a vial, and when said door is in a closed position, a vial retention zone is defined between said second open end of said vial retention section and said wall member.

16. A vial holder according to claim 15, wherein said handle portion is substantially cylindrically shaped.

17. A vial holder according to claim 15, further comprising a plurality of aligning elements positioned on said internal wall of said vial retention section for alignment of a vial within said vial retention section.

18. A vial holder according to claim 17, wherein said plurality of aligning elements are a plurality of positioning vanes which extend in the direction of the longitudinal axis of said vial retention section.

19. A vial holder according to claim 15, wherein said vial retention section is transparent.

20. A vial holder according to claim 15, further comprising a magnifying lens integral with said vial retention section.

21. A vial holder according to claim 15, wherein said handle portion exhibits a flat surface extending in the direction of said longitudinal axis of said handle portion.

22. A vial holder according to claim 15, wherein said handle portion exhibits a concave surface extending in the direction of said longitudinal axis of said handle portion.

23. A vial holder according to claim 15, further comprising spring elements attached to the internal wall of said vial retention section wherein said spring elements are capable of engaging a vial positioned within said vial retention section.

24. A vial holder according to claim 15, further comprising:

a second hollow vial retention section having a hollow interior attached to said second end of said handle portion, said second end of said handle portion being closed by a second wall member, said second hollow vial retention section having a longitudinal axis, a substantially cylindrically shaped internal wall, a first open end adjacent said second end of said handle portion and a second open end;

at least one additional retention member for preventing passage of a vial, when positioned within said second vial retention section, through said second open end of said second vial retention section;

means for displacing said second wall member of said handle portion and said second vial retention section from one another whereby access is provided into the hollow interior of said second vial retention section for introduction of a vial; and said second wall member of said handle portion is connected to said door;

wherein, when said door is in an open position, access is provided into the interior of said second vial retention section for introduction of a vial; and when said door is in a closed position, a vial retention zone is defined between said second open end of said second vial retention section and said second wall member.

25. A vial holder according to claim 24, further comprising:

a plurality of aligning elements positioned on said internal wall of said vial retention section for alignment of a vial within said vial retention section; and a plurality of additional aligning elements positioned on said internal wall of said second vial retention section for alignment of a vial within said second vial retention section.

26. A vial holder according to claim 1 in combination with at least one vial, and at least one syringe, to define a vial holder kit.

27. A vial holder according to claim 15 in combination with at least one vial, and at least one syringe, to define a vial holder kit.

28. A vial holder according to claim 1, wherein said means for displacing permits movement of said vial retention section, while attached to said handle portion, between a first position, in which its longitudinal axis is substantially aligned with said longitudinal axis of said handle portion and a second position in which its longitudinal axis is displaced from that of said handle portion.

29. A vial holder according to claim 4, wherein said at least one retention member is a tab positioned at the end of each of said positioning vanes adjacent said second open end of said vial retention section.

30. A vial holder according to claim 18, wherein said at least one retention member is a tab positioned at the end of each of said positioning vanes adjacent said second open end of said vial retention section.

31. A vial holder comprising:

a hollow vial retention section having a hollow interior and a longitudinal axis, substantially cylindrically shaped internal wall, a first open end, a second open end, and at least one retention member for preventing passage of a vial through said second open end of said vial retention section;

a handle portion having a longitudinal axis, a first end and a second end;

said vial retention section being attached to said handle portion wherein said handle portion is positioned beneath said vial retention section in the direction of the longitudinal axis of said vial retention section;

a wall member provided at said first end of said handle portion wherein said wall member separates said handle portion from said vial retention section; and means for displacing said wall member of said handle portion and said vial retention section from one another, whereby access is provided into the hollow interior of said vial retention section for introduction of a vial.

32. A vial holder comprising:

a handle portion having a longitudinal axis, a first end and a second end, wherein at least said first end of said handle portion is closed by a wall member;

a hollow vial retention section having a hollow interior, attached to said first end of said handle portion, said vial retention section having a longitudinal axis, a substantially cylindrically shaped internal wall, a first open end adjacent said first end of said handle portion, and a second open end;

at least one retention member for preventing passage of a vial, when positioned within said vial retention section, through said second open end of said vial retention section; and means for displacing said wall member of said handle portion and said vial retention section from one another whereby access is provided into the hollow interior of said vial retention section for introduction of a vial;

wherein said means for displacing is a pivotal hinge connecting said vial retention section with said handle portion, whereby said vial retention section is pivotally attached to said handle portion to permit access into the interior of said vial retention section through said first open end.

33. A vial holder comprising:

a handle portion having a longitudinal axis, a first end and a second end, wherein at least said first end of said handle portion is closed by a wall member;

a hollow vial retention section having a hollow interior, attached to said first end of said handle portion, said vial retention section having a longitudinal axis, a substantially cylindrically shaped internal wall, a first open end adjacent said first end of said handle portion, and a second open end;

at least one retention member for preventing passage of a vial, when positioned within said vial retention section, through said second open end of said vial retention section;

a second hollow vial retention section having a hollow interior attached to said second end of said handle portion, said second end of said handle portion being closed by a second wall member, said second hollow vial retention section having a longitudinal axis, a substantially cylindrically shaped internal wall, a first open end adjacent said second end of said handle portion and a second open end;

at least one additional retention member for preventing passage of a vial, when positioned within said second vial retention section, through said second open end of said second vial retention section; and means for displacing said wall member of said handle portion and said vial retention section from one another and for displacing said second wall member and said second vial retention section from one another, whereby access is provided into the hollow interior of said vial retention section and into the hollow interior of said second vial retention section for introduction of vials.

* * * * *